(12) United States Patent
Roschke et al.

(10) Patent No.: US 9,982,763 B2
(45) Date of Patent: May 29, 2018

(54) ELECTRICALLY POWERED DRIVE SYSTEM FOR MEDICAL DEVICE

(71) Applicant: JOHNSON ELECTRIC S.A., Murten (CH)

(72) Inventors: Thomas Roschke, Hong Kong (CN); Carl Henric Andreas Svennsson, Shenzhen (CN)

(73) Assignee: JOHNSON ELECTRIC S.A., Murten (CH)

( * ) Notice: Subject to any disclaimer, the term of this patent is extended or adjusted under 35 U.S.C. 154(b) by 887 days.

(21) Appl. No.: 14/502,904

(22) Filed: Sep. 30, 2014

(65) Prior Publication Data

US 2015/0090058 A1 Apr. 2, 2015

(30) Foreign Application Priority Data

Sep. 30, 2013 (CN) .......................... 2013 1 0465511

(51) Int. Cl.

| F16H 21/18 | (2006.01) |
|---|---|
| A61B 17/068 | (2006.01) |
| F16H 19/02 | (2006.01) |
| F16H 21/26 | (2006.01) |
| F16H 21/50 | (2006.01) |
| A61B 17/00 | (2006.01) |
| A61B 17/32 | (2006.01) |
| A61B 17/29 | (2006.01) |
| A61B 17/072 | (2006.01) |

(52) U.S. Cl.
CPC ........... *F16H 21/18* (2013.01); *A61B 17/068* (2013.01); *F16H 19/02* (2013.01); *F16H 21/26* (2013.01); *F16H 21/50* (2013.01); *A61B 2017/00398* (2013.01); *A61B 2017/07285* (2013.01); *A61B 2017/2913* (2013.01); *A61B 2017/320028* (2013.01); *Y10T 74/18248* (2015.01)

(58) Field of Classification Search
CPC .......... F16H 21/18; F16H 21/32; F16H 19/02; F16H 21/26; F16H 21/50; Y10T 74/18248; A61B 17/068; A61B 2017/00398; A61B 2017/07285; A61B 2017/2913; A61B 2017/320028
USPC ....................... 227/175.1, 131; 74/50, 47, 54
See application file for complete search history.

(56) References Cited

U.S. PATENT DOCUMENTS 3,049,803 A * 8/1962 Danger .................... A01G 3/00
30/228
4,038,721 A * 8/1977 Kendzior ............... A22B 5/207
30/394

(Continued)

*Primary Examiner* — Michelle Lopez
(74) *Attorney, Agent, or Firm* — Muncy, Geissler, Olds & Lowe, P.C.

(57) ABSTRACT

An electrically powered drive system for a medical device includes a motor, a gear box driven by the motor, a driving member for moving a part of the device, a crank mechanism, and a push-pull mechanism. The crank mechanism includes first and second crank arms each having a connection end and a distal end. The first crank arm's distal end is pivotally connected to the driving member. The second crank arm's connection end is pivotally connected to the first crank arm's connection end. The second crank arm's distal end is pivotally connected to a stationary member. The push-pull mechanism is connected to and driven by an output member of the gear box to drive the crank mechanism to move the driving member between a retracted position and an extended position.

13 Claims, 3 Drawing Sheets

(56) References Cited

U.S. PATENT DOCUMENTS

| | | | | |
|---|---|---|---|---|
| 4,936,845 A | * | 6/1990 | Stevens | A61B 17/320758 604/22 |
| 5,237,884 A | * | 8/1993 | Seto | B27B 19/006 30/166.3 |
| 5,533,661 A | | 7/1996 | Main et al. | |
| 6,745,638 B1 | * | 6/2004 | Godtner | B21J 9/18 74/44 |
| 8,028,885 B2 | | 10/2011 | Smith et al. | |
| 8,573,459 B2 | | 11/2013 | Smith et al. | |
| 8,636,736 B2 | | 1/2014 | Yates et al. | |
| 2011/0017801 A1 | | 1/2011 | Zemlok et al. | |
| 2011/0224754 A1 | | 9/2011 | Wei | |
| 2015/0090058 A1 | * | 4/2015 | Roschke | F16H 19/02 74/49 |

* cited by examiner

ELECTRICALLY POWERED DRIVE SYSTEM FOR MEDICAL DEVICE

CROSS REFERENCE TO RELATED APPLICATIONS

This non-provisional patent application claims priority under 35 U.S.C. § 119(a) from Patent Application No. 201310465511.6 filed in The People's Republic of China on Sep. 30, 2013, the entire contents of which are incorporated herein by reference.

FIELD OF THE INVENTION

This invention relates to a medical device and in particular, to an electrically powered drive system for a medical device, such as a surgical stapler or surgical cutter.

BACKGROUND OF THE INVENTION

Conventional surgical staplers are manually operated, which imposes a high physical requirement for a surgeon to operate. For example, hard manual work can reduce surgeon's focus on other important points like positioning of the device, compression of tissue etc. An electrically powered drive system was thus developed to address this problem. For example, U.S. Pat. No. 8,028,885 proposes to drive a surgical stapler based on a motor-driven leadscrew mechanism. However, the leadscrew produces a drive force that is constant independent of the travel of the surgical stapler. In order to ensure a large force at the end of the travel of the surgical stapler, the leadscrew has to provide a large drive force through the entire range of travel. As such, the motor has to maintain a high output torque and therefore has a low efficiency.

SUMMARY OF THE INVENTION

Thus there is a desire for an improved electrically powered drive system for a medical device which can address the problem described above.

Accordingly, in one aspect thereof, the present invention provides an electrically powered drive system for a medical device, including a motor, a gear box, a driving member, a crank mechanism, and a push-pull mechanism. The gear box is driven by the motor and includes an output member. The driving member is configured to move a part of the medical device. The crank mechanism includes a first crank arm and a second crank arm pivotally connected to the first crank arm. The first crank arm has a connection end and a distal end. The distal end of the first crank arm is pivotally connected to the driving member. The second crank arm has a connection end and a distal end. The connection end of the second crank arm is pivotally connected to the connection end of the first crank arm. The distal end of the second crank arm is pivotally connected to a stationary member. The push-pull mechanism is connected between the gear box and the crank mechanism. The push-pull mechanism is connected to the output member of the gear box. The push-pull mechanism is configured to drive the crank mechanism to move the driving member between a retracted position and an extended position under the drive of the output member.

Preferably, the push-pull mechanism includes a cam connected to the output member of the gear box, and the movement of the driving member between the retracted position and the extended position results from a movement of the cam between a first position and a second position.

Preferably, the push-pull mechanism further includes a push-pull arm having one end connected to the crank mechanism and the other end connected to and drivable by the cam.

Preferably, the one end of the push-pull arm is connected to a joint between the first crank arm and the second crank arm.

Preferably, the other end of the push-pull arm defines an opening in which the cam is received.

Alternatively, when the driving member is at the retracted position, a joint between the first and second crank arms of the crank mechanism sinks below the distal ends of the first and second crank arms so that an angle is formed between the first and second crank arms, and the cam is located outside the angle.

Alternatively, the cam is located outside an angle formed between the first crank arm and the second crank arm of the crank mechanism and abuts against one of the first crank arm and the second crank arm, and the push-pull mechanism further includes a resilient element for returning the crank mechanism to its initial state.

Alternatively, the push-pull mechanism includes a wheel connected to the output member of the gear box and a cable, one end of the cable being fixed to the wheel, and the other end of the cable being connected to the crank mechanism.

Preferably, the push-pull mechanism further includes a resilient element for returning the crank mechanism to its initial state.

Preferably, the stationary member to which the distal end of the second crank arm is pivotally connected is a housing of the gear box.

Preferably, when the driving member is at the extended position, the angle between the first crank arm and the second crank arm is less than 180 degrees.

Preferably, the first crank arm has a greater length than the second crank arm.

Alternatively, the first crank arm and the second crank arm are of equal length.

Preferably, the cam is formed as an off-center pin on the output member.

Preferably, the medical device is a surgical stapler or a surgical cutter.

BRIEF DESCRIPTION OF THE DRAWINGS

Preferred embodiments of the invention will now be described, by way of example only, with reference to figures of the accompanying drawings. In the figures, identical structures, elements or parts that appear in more than one figure are generally labeled with a same reference numeral in all the figures in which they appear. Dimensions of components and features shown in the figures are generally chosen for convenience and clarity of presentation and are not necessarily shown to scale. The figures are listed below.

DETAILED DESCRIPTION OF THE PREFERRED EMBODIMENTS

As this invention is particularly suited for use in surgical staplers and surgical cutters, the invention will be described as applied to surgical stapler or cutter. However, it should be noted that the invention may be applied to other medical devices.

Figure 1:
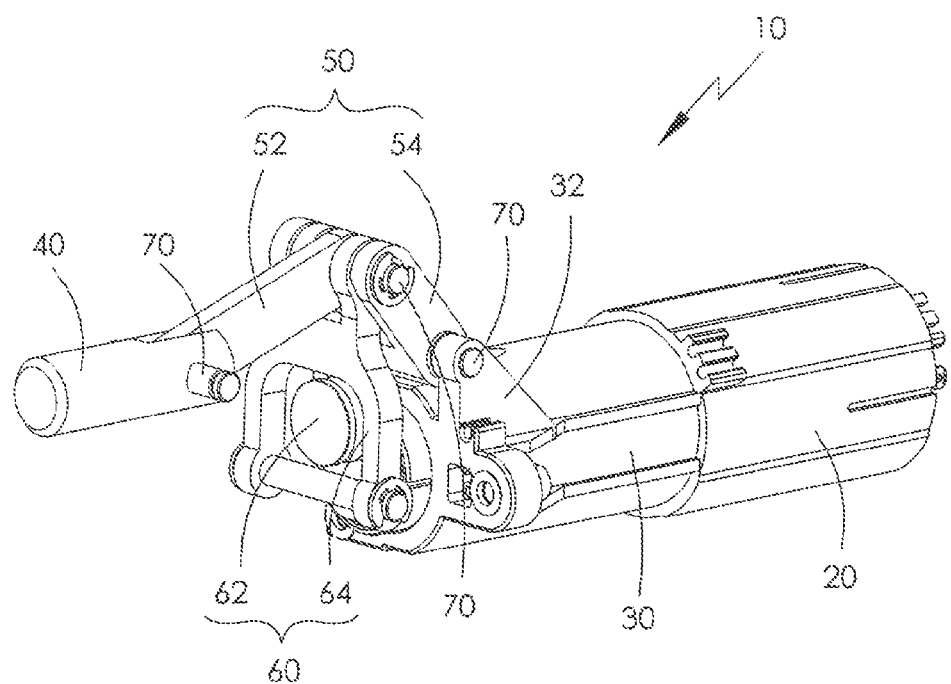
FIG. 1 is a perspective view of an electrically powered drive system for a medical device according to a preferred embodiment of the present invention.
Figure 2:
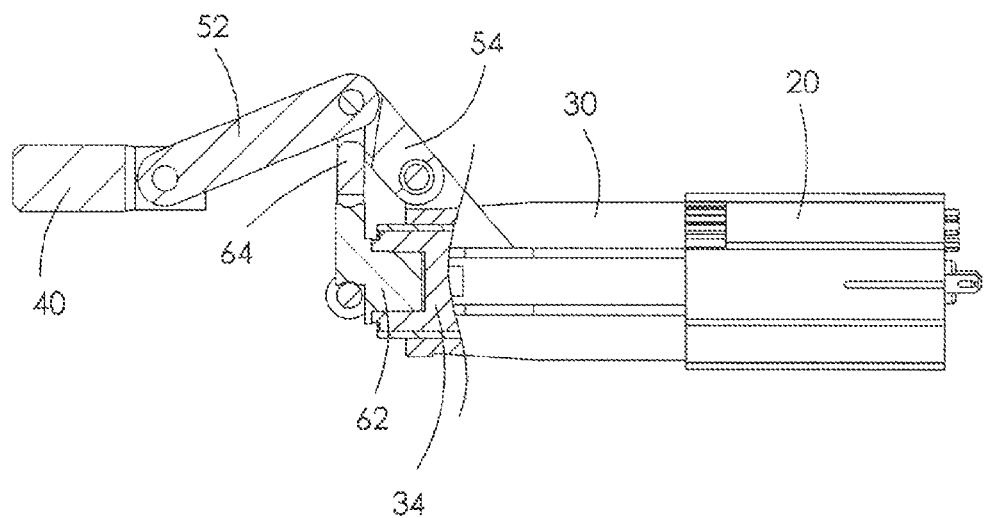
FIG. 2 is a partial sectional view of the electrically powered drive system of FIG. 1, with a driving member at a retracted position.
Figure 3:
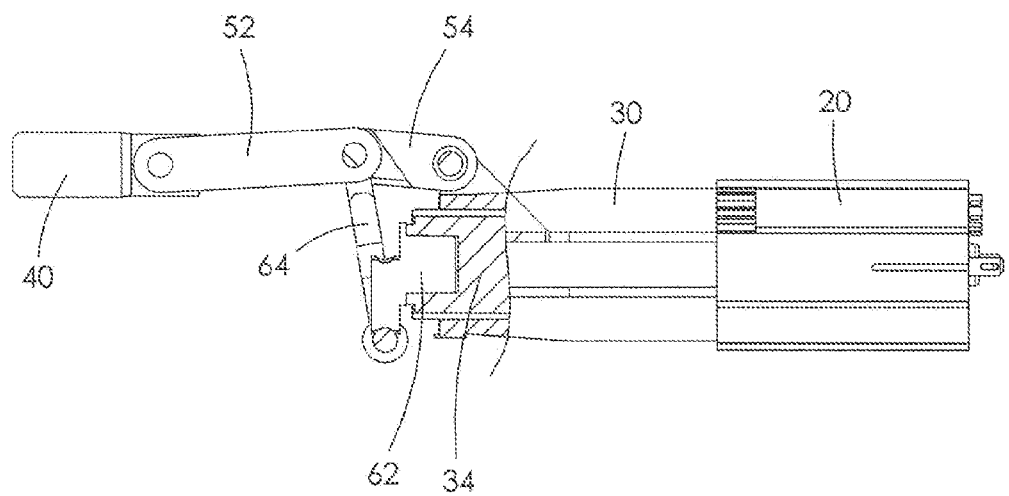
FIG. 3 is a partial sectional view of the electrically powered drive system of FIG. 1, with the driving member at an extended position.

Referring to FIG. 1 to FIG. 3, an electrically powered drive system 10 for a medical device in accordance with a first preferred embodiment of the present invention includes a motor 20, a gear box 30 driven by the motor 20, a driving member 40, a crank mechanism 50, and a push-pull mechanism 60 connected between the gear box 30 and the crank mechanism 50.

The motor 20 may be any known motor. Preferably, the motor 20 is a direct current brush motor and may be battery powered, which is especially suitable for the electrically powered drive system 10 for a handheld medical device.

The gear box 30 is preferably a planetary gear box including a housing, multiple stages of planetary gears (not shown) mounted inside the housing, and an output shaft 34.

The driving member 40 is preferably a driving rod. The driving rod 40 has a distal end that may be connected with a movable part of the medical device, such as the surgical stapler or surgical cutter 80 (see FIG. 4) for driving the surgical stapler or surgical cutter 80 to move. During operation, the driving member 40 can only make a linear slide movement under the constraint of the surgical device.

The crank mechanism 50 includes a first crank arm 52 and a second crank arm 54 that are pivotally connected with an angle formed there between. Each of the first crank arm 52 and the second crank arm 54 has a connection end and a distal end. The distal end of the first crank arm 52 (including the portion adjacent the distal end) is pivotally connected to the driving member 40. Specifically, the distal end of the first crank arm 52 has a through hole. A cutout is defined in one end of the driving member 40 adjacent the first crank arm 52, for receiving the distal end of the first crank arm 52. The driving member 40 has through holes in opposite sides of the cutout, which align with the through hole of the first crank arm 52. A connection pin 70 passes through the through holes of the driving member 40 and the first crank arm 52 thus pivotally connecting the first crank arm 52 to the driving member 40. The connection end of the second crank arm 54 is pivotally connected with the connection end of the first crank arm 52 by means of another connection pin 70, and the distal end of the second crank arm 54 is pivotally connected with a stationary member 32 by means of a further connection pin 70. As such, the second crank arm 54 is pivotable about its distal end. The stationary member may be a stationary housing of any mechanism or another mounting structure. In this embodiment, the stationary member 32 is the housing of the gear box 30.

Preferably, the length of the first crank arm is greater than the length of the second crank arm. In this embodiment, the length of the first crank arm 52 is at least 1.3 times of the length of the second crank arm 54. Alternatively, the length of the first crank arm 52 may be equal to the length of the second crank arm 54.

In this embodiment, the push-pull mechanism 60 includes a cam 62 and a push-pull arm 64. The cam 62 is connected to and thus driven by the output shaft 34 of the gear box 30. One end of the push-pull arm 64 is connected to the crank mechanism 50, and the other end of the push-pull arm 64 is connected to the cam 62. Specifically, one end of the push-pull arm 64 forms a through hole aligning with the through holes of the first and second crank arms 52, 54. The first and second crank arms 52, 54 and the push-pull arm 64 are connected together by passing the pin 70 through the holes of the first and second crank arms 52, 54 as well as the hole of the push-pull arm 64. The other end of the push-pull arm 64 forms an opening in which the cam 62 is received.

The operating principle of this electrically powered drive system will now be described.

When the electrically powered drive system 10 is in an initial state, with the motor turned off, the angle between the first crank arm 52 and the second crank arm 54 of the crank mechanism 50 (the term "the angle between the first crank arm 52 and the second crank arm 54" described herein refers to the angle that is less than or equal to 180 degrees) is an obtuse angle. Preferably, the angle is about 110 degrees. The push-pull arm 64 is located within the angle between the first crank arm 52 and the second crank arm 54 of the crank mechanism 50. The cam 62 is in a non-working state, and a farthest end of the cam 64 from the cam's centerline of rotation is at a position close to the crank mechanism 50. The driving member 40 is at a retracted position as shown in FIG. 2.

When the motor 20 is operated, the motor rotates the cam 62 through the gear box 30, which causes the farthest end of the cam 62 from the cam's centerline of rotation to gradually move away from the crank mechanism 50. In this embodiment, the cam 62 is rotated an angle of 180 degrees and, as such, the farthest end of the cam 62 from the cam's centerline of rotation is rotated to a position away from the crank mechanism 50 as shown in FIG. 3. The cam 62 during the course of rotation pulls the push-pull arm 64 to move away from the joint between the first and second crank arms 62, 64 (move downwardly as shown in the drawing), which in turn pulls the joint between the first and second crank arms 62, 64 downwardly, such that the angle between the first and second crank arms 62, 64 increases. The distal end of the second crank arm 54 is pivotally connected to the stationary member 32 and cannot make a displacement and, as a result, the distal end of the first crank arm 52 is caused to move in a direction away from the second crank arm 54 (move leftwards as shown), thereby pushing the driving member 40 to advance to the extended position. Accordingly, the movable part of the surgical stapler or cutter 80 connected to the driving member 40 is driven to a working position.

When an operation is completed, the motor 20 rotates to drive the cam 62 to the initial position, such that the push-pull arm 64 pushes the joint between the first and second crank arms 52, 54 upwardly. As a result, the angle between the first and second crank arms 52, 54 gradually decreases, and the distal end of the first crank arm 52 moves in a direction toward the second crank arm 54, thereby pulling the driving member 40 back to its retracted position. Understandably, the motor 20 may be reversed or continue to rotate further in its original direction, such that the cam 62 returns to the initial position by rotating through a further 180 degrees to reach the original orientation.

Preferably, the distance between the retracted position and extended position, i.e. the travel, of the driving member 40 is 5 to 10 millimeters, and the change in value of the angle between the first crank arm 52 and the second crank arm 54 is 60 to 70 degrees. When the driving member 40 is at the extended position, in order to avoid self-locking of the crank mechanism 50, the angle between the first crank arm 52 and the second crank arm 54 of the crank mechanism 50 is preferably less than 180 degrees. In this embodiment, when the driving member 40 is at the extended position, the angle between the first crank arm 52 and the second crank arm 54 of the crank mechanism 50 is 175 degrees.

Understandably, corresponding to the travel of the driving member 40, the rotation angle of the cam 62 is not intended to be limited to 180 degrees and can be another value according to actual requirements. Also the cam may be in the form of an off-center pin formed on or fitted to the output member of the gearbox.

Figure 4:
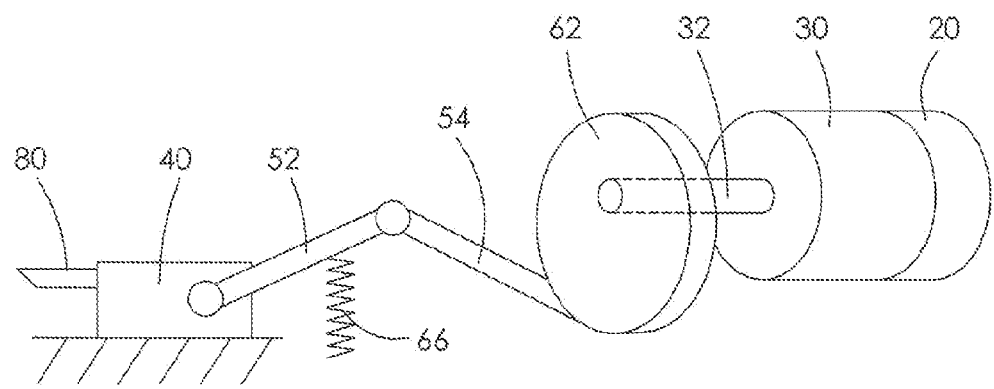
FIG. 4 is a schematic representation of an electrically powered drive system for a medical device according to a second embodiment of the present invention.

FIG. 4 is a schematic representation of an electrically powered drive system for a medical device according to a second embodiment. In this embodiment, the push-pull mechanism 60 includes a cam 62 and a resilient element such as a spring 66. The cam 62 is located outside the angle between the first and second crank arms 52, 54 and bears against the second crank arm 54. One end of the spring 66 is connected to the first crank arm 52 or the second crank arm 54, and the other end is fixed. When the motor 20 operates, the cam 62 is rotated by the gear box 30, which in turn directly drives the second crank arm 54 to rotate about its distal end, thus causing an increase of the angle between the first and second crank arms 52, 54 and resilient deformation of the spring 66. In this embodiment, the resilient deformation of the spring 66 is compressive deformation. The distal end of the first crank arm 52 is caused to move in a direction away from the second crank arm 54, thereby pushing the driving member 40 to advance to the extended position.

When an operation is completed, the motor 20 is reversed to return the cam 62 to its initial state, which allows the spring 66 to return back to its original state and thus push the first crank arm 52 upwardly. As a result, the angle between the first and second crank arms 52, 54 decreases, and the distal end of the first crank arm 52 is caused to move in a direction toward the second crank arm 54, thereby pulling the driving member 40 back to the initial or retracted position. Understandably, the cam 62 may also directly bear against the first crank arm 52 or a joint between the first and second crank arms 52, 54, and the spring 66 may also experience an extensional deformation during operation of the crank mechanism 50. It should also be understood that the return spring 66 may be disposed at various positions as long as it can return the driving member 40 to the initial position. For example, the return spring 66 may be connected to either one of the second crank arm 54, the connection pin 70 and the driving member 40. Also, depending on the design of the cam, the motor may continue to rotate in the same direction to return the cam to the initial position.

Figure 5:
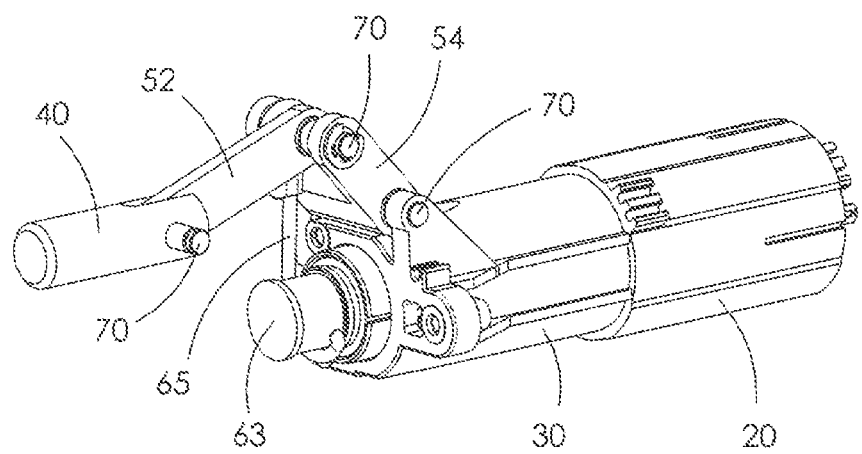
FIG. 5 illustrates an electrically powered drive system for a medical device according to another embodiment of the present invention.

FIG. 5 illustrates an electrically powered drive system for a medical device according to another embodiment. In this embodiment, the push-pull mechanism 60 includes a wheel 63, a cable 65, and a resilient element such as the spring 66 (see FIG. 4). The wheel 63 is connected to and rotatable with the output shaft 34 of the gear box 30. One end of the cable 65 is fixed to and wound around the wheel 63, and the other end of the cable 65 is fixed to the crank mechanism 50. In this embodiment, the other end of the cable 65 is fixed to a joint between the first and second crank arms 52, 54, i.e. at the connection pin 70, of the crank mechanism 50. When the motor 20 operates to rotate the wheel 63, the cable 65 is further wound around the wheel 63 and therefore pulls the joint of the crank mechanism 50 downwardly, such that the angle between the first and second crank arms 52, 54 increases, and the distal end of the first crank arm 52 moves in a direction away from the second crank arm 54, thereby pushing the driving member 40 to slide to the extended position. When the operation is completed, the motor 20 rotates in the reverse direction to release the cable 65, which allows the spring 66 to return back to its original state and thus push the first crank arm 52 upwardly. As a result, the angle between the first and second crank arms 52, 54 decreases, and the distal end of the first crank arm 52 is caused to move in a direction towards the second crank arm 54, thereby pulling the driving member 40 back to the initial position, i.e. the retracted position. It should be understood that the return spring 66 may be disposed at various positions. For example, the return spring 66 may be connected to the second crank arm 54, the connection pin 70 or the driving member 40.

Figure 6:
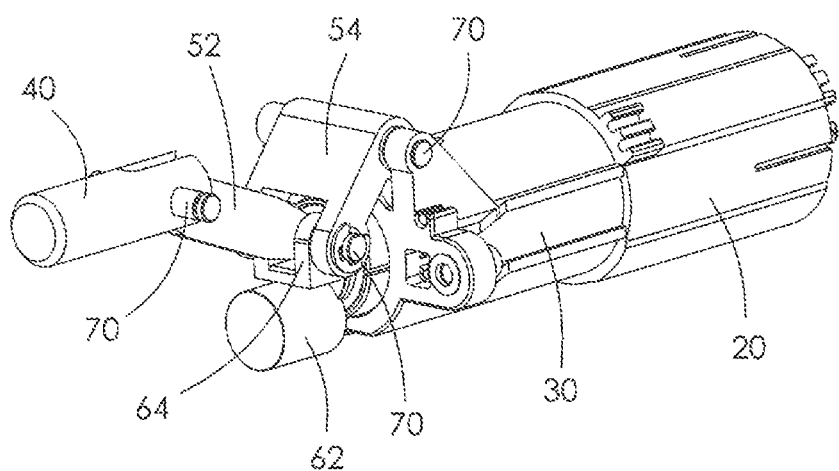
FIG. 6 illustrates an electrically powered drive system for a medical device according to a further embodiment of the present invention.

FIG. 6 illustrates an electrically powered drive system 10 for a medical device according to a further embodiment. In this embodiment, the push-pull mechanism 60 includes a cam 62 and a push-pull arm 64. The cam 62 is connected to and thus driven by the output shaft 34 of the gear box 30. In this embodiment, one end of the push-pull arm 64 is connected to the crank mechanism 50, for example, the connection pin 70 of the crank mechanism 50, and the other end of the push-pull arm 64 bears against or is otherwise connected to an outer surface of the cam 62. When the electrically powered drive system is in the initial state, due to gravity, the connection ends of the first and second crank arms 52, 54 of the crank mechanism 50 sink below the distal ends of the first and second crank arms 52, 54 so that an angle is formed between the first and second crank arms 52, 54. The cam 62 and push-pull arm 64 are both located outside the angle between the first and second crank arms 52, 54, and the farthest end of the cam 62 from the cam's centerline of rotation is at a position away from the crank mechanism 50. When the motor 20 operates, the cam 62 is driven by the gear box 30, which causes the farthest end of the cam 62 from the cam's centerline of rotation to gradually move closer to the crank mechanism 50 and causes the outer surface of the cam 62 to push the push-pull arm 64 upwardly, such that the angle between the first and second crank arms 52, 54 increases. As a result, the distal end of the first crank arm 52 is caused to move in a direction away from the second crank arm 54, thereby pushing the driving member 40 to advance to the extended position. When the operation is completed, the motor 20 rotates the cam 62 to the initial position and the crank mechanism 50 sinks due to gravity or to the connection between the cam and the push-arm. As a result, the angle between the first and second crank arms 52, 54 decreases, and the distal end of the first crank arm 52 moves in a direction toward the second crank arm 54, thereby pulling the driving member 40 back to its retracted position. Understandably, the motor 20 may either rotate in the reverse direction or rotate further in its original direction, such that the cam 62 returns to the initial position. The rotation angle of the cam 62 may be adjusted according to actual requirements.

Compared to the manual operation of the prior art, the electrically powered drive system for a medical device of the present invention is simpler to operate, labor-saving and can achieve more precise control of stapling and cutting movement. Compared to the leadscrew-based operation of the prior art, the electrically powered drive system for a medical device of the present invention utilizes a crank mechanism having a pair of pivotally connected crank arms 52, 54. With this design, the output torque of the motor 20 can be amplified and transmitted to the driving member 40. At the beginning of the travel of the driving member 40, the crank mechanism 50 transmits a relatively small drive force to the driving member 40. The drive force of the crank mechanism 50 to the driving member 40 gradually increases as the distance travelled increase. This drive force is transmitted to the surgical stapler or cutter. As such, the drive force that the crank mechanism 50 applies to the driving member 40 is much better adapted to the force requirements of the surgical stapler or cutter. Therefore, the motor 20 itself is not required to provide a large output torque, which can reduce the amount of energy wasted.

In the description and claims of the present application, each of the verbs "comprise", "include", "contain" and "have", and variations thereof, are used in an inclusive sense, to specify the presence of the stated item but not to exclude the presence of additional items.

Although the invention is described with reference to one or more preferred embodiments, it should be appreciated by those skilled in the art that various modifications are possible. Therefore, the scope of the invention is to be determined by reference to the claims that follow.

The invention claimed is:

1. An electrically powered drive system for a medical device, comprising:
   a motor;
   a gear box driven by the motor and comprising an output member;
   a driving member configured to move a movable part of the medical device;
   a crank mechanism comprising:
      a first crank arm having a connection end and a distal end, the distal end of the first crank arm being pivotally connected to the driving member; and
      a second crank arm having a connection end and a distal end, the connection end of the second crank arm being pivotally connected to the connection end of the first crank arm, and the distal end of the second crank arm being pivotally connected to a stationary member; and
   a push-pull mechanism connected between the gear box and the crank mechanism, the push-pull mechanism being connected to the output member of the gear box, the push-pull mechanism being configured to drive the crank mechanism to move the driving member between a retracted position and an extended position under the drive of the output member;
   wherein when the driving member is at the extended position, the angle between the first crank arm and the second crank arm is less than 180 degrees.

2. The drive system of claim 1, wherein the push-pull mechanism comprises a cam connected to the output member of the gear box, and the movement of the driving member between the retracted position and the extended position results from a movement of the cam between a first position and a second position.

3. The drive system of claim 2, wherein the push-pull mechanism further comprises a push-pull arm having one end connected to the crank mechanism and the other end connected to and drivable by the cam.

4. The drive system of claim 3, wherein the one end of the push-pull arm is connected to a joint between the first crank arm and the second crank arm.

5. The drive system of claim 3, wherein the other end of the push-pull arm defines an opening in which the cam is received.

6. The drive system of claim 2, wherein the cam is located outside an angle formed between the first crank arm and the second crank arm of the crank mechanism and abuts against one of the first crank arm and the second crank arm, and the push-pull mechanism further comprises a resilient element for returning the crank mechanism.

7. The drive system of claim 2, wherein when the driving member is at the retracted position, a joint between the first and second crank arms of the crank mechanism sinks below the distal ends of the first and second crank arms so that an angle is formed between the first and second crank arms, and the cam is located outside the angle.

8. The drive system of claim 1, wherein the push-pull mechanism comprises a wheel connected to the output member of the gear box and a cable, one end of the cable is fixed to the wheel, and the other end of the cable is connected to the crank mechanism.

9. The drive system of claim 8, wherein the push-pull mechanism further comprises a resilient element for returning the crank mechanism.

10. The drive system of claim 1, wherein the stationary member is a housing of the gear box.

11. The drive system of claim 1, wherein the first crank arm has a greater length than the second crank arm.

12. The drive system of claim 1, wherein the cam is an off-center pin on the output member.

13. The drive system of claim 1, wherein the medical device is a surgical stapler or a surgical cutter.

* * * * *